(12) United States Patent
Pallingen

(10) Patent No.: US 7,023,548 B2
(45) Date of Patent: Apr. 4, 2006

(54) PHOTOELECTRIC MEASURING DEVICE

(75) Inventor: Hans Pallingen, Brixen (IT)

(73) Assignee: VIPTRONIC GmbH, Brixen (IT)

(*) Notice: Subject to any disclaimer, the term of this patent is extended or adjusted under 35 U.S.C. 154(b) by 25 days.

(21) Appl. No.: 10/177,714

(22) Filed: Jun. 21, 2002

(65) Prior Publication Data
US 2003/0234930 A1 Dec. 25, 2003

(51) Int. Cl.
*G01J 4/00* (2006.01)

(52) U.S. Cl. ........................ 356/369; 356/402

(58) Field of Classification Search ................ 356/425, 356/445–448, 364–369, 402–419; 359/501
See application file for complete search history.

(56) References Cited

U.S. PATENT DOCUMENTS

| | | | |
|---|---|---|---|
| 3,834,817 A * | 9/1974 | Vinnemann et al. | 356/308 |
| 4,003,660 A * | 1/1977 | Christie, Jr. et al. | 356/407 |
| 4,575,249 A * | 3/1986 | Grieger | 356/369 |
| 4,670,744 A | 6/1987 | Buzak | |
| 5,129,726 A * | 7/1992 | Nielsen | 356/402 |
| 5,469,279 A | 11/1995 | Sharp et al. | |
| 5,726,755 A * | 3/1998 | Wolff | 356/364 |
| 5,754,921 A * | 5/1998 | Imaizumi et al. | 399/52 |
| 5,785,041 A * | 7/1998 | Weinstein et al. | 600/407 |
| 5,854,680 A * | 12/1998 | Rakitsch | 356/406 |
| 5,892,612 A | 4/1999 | Miller et al. | |
| 5,963,332 A * | 10/1999 | Feldman et al. | 356/425 |
| 6,055,053 A * | 4/2000 | Lesniak | 356/366 |
| 2002/0075482 A1* | 6/2002 | Pallingen | 356/446 |

FOREIGN PATENT DOCUMENTS

| | | |
|---|---|---|
| DE | 19530185 | 5/1996 |
| JP | 02189408 | 7/1990 |

OTHER PUBLICATIONS

European Search Report dated Mar. 11, 2002 (no translation).

* cited by examiner

*Primary Examiner*—Hoa Q. Pham
(74) *Attorney, Agent, or Firm*—McCarter & English, LLP

(57) ABSTRACT

A device for the density or colorimetric measurement of a measured object, i.e., a densitometer or colorimeter, comprising a light source for directing measurement light onto an object to be measured, a polarization filter positioned between the light source and the object to be measured, a photoelectric sensor, a second polarization filter positioned between the object to be measured and the sensor, at least one of the polarization filters for electronic control of polarization plane orientation, a measurement lens for directing the measurement light originating from a measurement location of the measured object through the second polarization filter and onto the sensor and a controller for electronically rotating the polarization plane for one of the polarization filters relative to the other by 90°.

6 Claims, 1 Drawing Sheet

PHOTOELECTRIC MEASURING DEVICE

FIELD OF THE INVENTION

The invention relates to measuring devices for the photoelectric measurement and relates in particular to a densitometer or a color measuring device.

BACKGROUND ART

Densitometric measuring devices and systems are often equipped with polarization filters. During measurements with polarization filters, a small color density decrease results during the drying of the printing ink and an expanded range in which the color density is linearly correlated with the layer thickness of the printing ink. When the measurement result is used for the machine control during printing, the printer has a large interest to obtain measurement values as long as possible before the color is dry in order to reduce waste. A polarization device is therefor necessary.

Wet printing inks have a shiny surface, while during drying the printing ink adapts to the surface structure of the paper and, depending on the paper quality, becomes more or less matte. This results in different measurement results before and after drying. The purpose of the polarization filter is to suppress the surface reflection of the wet print. Two polarization filters are used therefor. A first polarization filter is positioned in the light path of the light source and therefore lets only one oscillation plane pass through. The oriented light rays are partially reflected at the color surface without a change in the oscillation plane. A second polarization filter is located in the light path of the sensor and is rotated 90° relative to the first filter so that the polarized light rays reflected on a smooth surface cannot pass this second polarization filter or are only partially let through by this second polarization filter. The light portion originating from the surface shine is thereby strongly or ideally totally surppressed and the sensor essentially measures only the unpolarized light portion.

In colorimetric measurement systems, the measured value relates to the human eye. Since measurements with polarization filters do not correlate with the impression of the observer, the standards require color measurements without polarization filters.

Many modern measurement devices offer both possibilities of measurement, namely density measurements and colorimetric measurements, for example according to CIEL*a*b* or CIEL*u*v*. Mechanical solutions are provided in those measurement devices with which the polarization filter effect can be switched on or off.

In a known measurement device, one of the two polarization filters is physically rotatedly positioned so that its polarization plane can be adjusted to be selectively perpendicular or parallel to that of the other polarization filter. At parallel orientation, the light portion of the surface shine can reach the sensor and the measured result corresponds to that of a measurement device without polarization filter. In contrast, at perpendicular orientation of the two polarization planes, the shine portion is filtered out as described. Solutions with physically rotatable polarization filters are however especially disadvantageous for several reasons when the measurement device or system is integrated into a printing machine. However, significant effort is required even with measurement tables or portable apparatus, to ensure that switching of the polarization filters is not forgotten.

SUMMARY OF THE INVENTION

Starting from this state of the art, it is now an object of the present invention to provide an improved measurement device wherein the filtering out of the shine related light portion can be activated or deactivated purely electronically, which means without mechanical movement of polarization filters or other components of the measurement device.

This object is achieved with a measuring device in accordance with the invention, wherein at least one of two polarization filters is constructed to be electronically controllable and is supplied by a control electronic with appropriate control voltages. The rotation of the polarization plane and thereby the activation or deactivation of the shine suppression can be achieved simply and quickly with electronic means by application of suitable electrical signals from the control electronic.

Thus, according to the present disclosure, a device for the photoelectric measurement of a measured object is constructed especially as densitometer or color measurement device, and includes a light source (1, 2) for exposure of the measured object (6) to measurement light, a polarization filter (8) located between the light source (1, 2) and the measured object (6), a photoelectric sensor (4), a second polarization filter (9) located between the measured object (6) and the sensor (4), a measurement lens (3) which directs the measurement light originating from a measurement location from the measurement object (6) through the second polarization filter (9) onto the sensor (4), and a control electronic (5) cooperating with the sensor (4) for the processing of the electrical signals produced thereby. At least one of the two polarization filters (9) is electronically controllable, whereby its polarization plane can be rotated by the control electronic (5) by 90° relative to that the other of the two polarization filters. The polarization filter(s) is (are) thereby constructed according to liquid crystal technology and preferably consist of several layers in order to reliably suppress light portions which are not located in the polarization plane. The rotation of the polarization plane and thereby the activation or deactivation of the shine suppression can be easily and quickly achieved purely electronically due to the electronically controllable construction of the polarization filter and by the application of suitable electrical signals.

BRIEF DESCRIPTION OF THE DRAWINGS

The invention will now be described in more detail by way of example only and with reference to the following drawings, wherein.

DETAILED DESCRIPTION OF THE PREFERRED EMBODIMENTS

Figure 1:
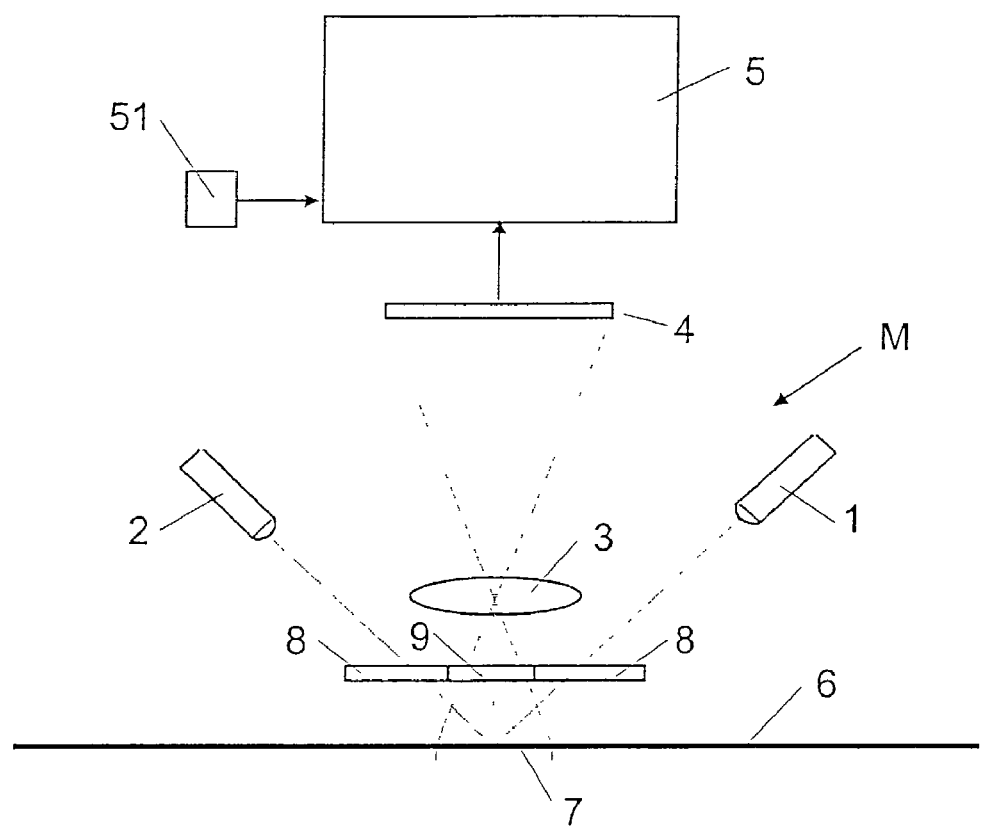
FIG. 1 is a principal schematic of a typical embodiment of the measurement device in accordance with the invention.

The measurement device schematically depicted in FIG. 1 (referred to in total by the reference M) is constructed as a remission measurement device and includes in a generally known manner a light source consisting of at least one lamp 1 (in this exemplary embodiment two lamps 1 and 2 are provided), a measurement lens 3, a photoelectric sensor 4 and a control electronic 5. Furthermore, a first polarization filter 8 is positioned between the lamps 1 and 2 and the object to be measured (object 6) and a second polarization filter 9 is provided between the measured object 6 and the measurement lens 3. As is common with measurement devices of this type, the lamps 1 and 2 transmit light through the first polarization filter 8 and illuminate at 45° a measurement field 7 of a measured object 6, and the measurement lens 3 captures the measurement light which is remitted from the measured object and passes through the second polarization filter 9 at 0° and directs such measurement light onto the sensor 4. The control electronic 5 converts the analog electrical signals produced by the sensor 4 corresponding to the intensity of the received light into corresponding digital measurement values and then calculates therefrom the desired measured quantity or provides the digital measured values to an external processor for further processing.

So far, the measurement device in accordance with the invention corresponds to conventional measurement devices of this type, so that the person skilled in the art does not require any further explanation in this respect.

The inventive difference relative to the prior art relates, at least in part, to the construction of the polarization filter 8 or filters 8 and 9. At least one of the two polarization filters 8 and 9, in the illustrated example the second polarization filter 9, is constructed in accordance with the present disclosure as an electronically controllable polarization plane. The electronically controllable polarization plane is advantageously realized by one or more polarizing liquid crystal layers, the polarization plane of which can be rotated by 90° under the influence of an electrical field. Suitable liquid crystals and technologies are, for example, those used in known liquid crystal displays (LCDs). Especially suited are so called twisted nematic liquid crystals, since they rotate the polarization plane by exactly 90° upon application of an appropriate electrical potential.

The control electronic 5 provides the control voltage required for operation of the second polarization filter. The rotation of the polarization plane and thereby the activation or deactivation of the shine suppression can be carried out easily and quickly in a purely electronic manner by the application of suitable electrical signals. The switching can thereby be initiated manually through control keys 51 or under program control.

Figure 2:
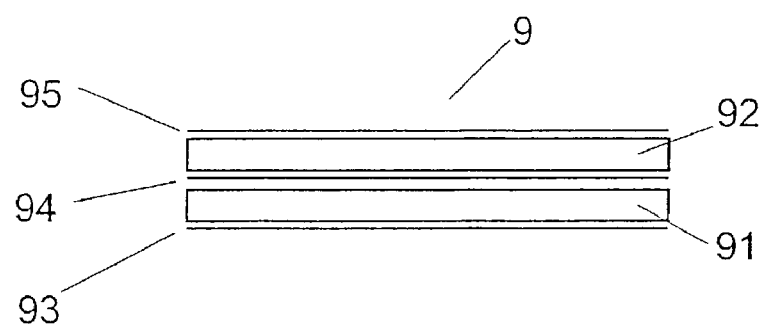
FIG. 2 is a schematical section through a polarization filter of a measurement device of FIG. 1.

A key parameter affecting the quality of the polarization relates to how strongly the (polarized) light portion which is not located in the polarization plane of the second polarization filter 9 is suppressed. In order to increase the quality of the liquid crystal polarization filter 9 in this regard, the polarization filter 9 can therefore have two or more sequentially arranged liquid crystal layers, as is illustrated by way of the schematic cross-section of FIG. 2.

The second polarization filter 9 includes two liquid crystal layers 91 and 92, which are sandwiched between three transparent electrodes 93–95. The three electrodes are connected to the control electronic 5 and are supplied thereby with suitable switching voltages in a known manner.

By complementing the disclosed instrumentation with color selective and/or spectrally resolving optical components, the shown measurement device can be constructed in a generally known manner as a densitometer or a color measurement device.

The invention claimed is:

1. A device for density or colorimetric measurement of a measured object, comprising a light source for directing measurement light onto an object to be measured, a first polarization filter positioned between the light source and the object to be measured, a photoelectric sensor, a second polarization filter positioned between the object to be measured and the photoelectric sensor, at least one of the two polarization filters being constructed for electronic control of polarization plane orientation, a measurement lens for directing the measurement light originating from a measurement location of the measured object through the second polarization filter and onto the photoelectric sensor, and means for electronically rotating the polarization plane for at least one polarization filter relative to that of the other polarization filter by 90°.

2. Device according to claim 1, wherein at least one of the two polarization filters has at least one liquid crystal layer as polarizing medium, the polarization plane of which is rotatable by 90° under the influence of an electrical field.

3. Device according to claim 2, wherein the at least one liquid crystal layer includes twisted nematic liquid crystals.

4. Device according to claim 1, wherein only the second polarization filter located between the measured object and the sensor is constructed to be electronically controllable.

5. Device according to claim 1, wherein the means for electronically rotating the polarization plane is a control electronic, and wherein the control electronic further cooperates with the photoelectric sensor for processing of signals produced thereby.

6. A device for density or colorimetric measurement of a measured object, comprising a light source for directing measurement light onto an object to be measured, a first polarization filter positioned between the light source and the object to be measured, a photoelectric sensor, a second polarization filter positioned between the object to be measured and the photoelectric sensor, at least one of the two polarization filters being constructed for electric control of polarization plane orientation, a measurement lens for directing the measurement light originating from a measurement location of the measured object through the second polarization filter and onto the photoelectric sensor, means for electronically rotating the polarization plane for at least one polarization filter relative to that of the other polarization filter by 90°, a control electronic providing a control voltage required for operation of at least one polarization filter being constructed for electric control of polarization plane orientation, and at least one control key for manually switching the polarization plane orientation of at least one polarization filter being constructed for electric control of polarization plane orientation.

* * * * *